United States Patent
Jennewine (10) Patent No.: US 8,502,682 B2
(45) Date of Patent: *Aug. 6, 2013

(54) SIGNAL CONVERTING CRADLE FOR MEDICAL CONDITION MONITORING AND MANAGEMENT SYSTEM

(75) Inventor: R. Curtis Jennewine, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/337,025

(22) Filed: Dec. 23, 2011

(65) Prior Publication Data

US 2012/0092168 A1    Apr. 19, 2012

Related U.S. Application Data

(63) Continuation of application No. 12/147,467, filed on Jun. 26, 2008, now Pat. No. 8,085,151.

(60) Provisional application No. 60/946,760, filed on Jun. 28, 2007.

(51) Int. Cl.
*G08B 23/00*    (2006.01)
(52) U.S. Cl.
USPC .................. 340/573.1; 340/540; 600/300
(58) Field of Classification Search
USPC ........................................ 340/573.1
See application file for complete search history.

(56) References Cited

U.S. PATENT DOCUMENTS

| | | |
|---|---|---|
| 2,755,036 A | 7/1956 | Mikko |
| 3,208,121 A | 9/1965 | Price |
| 3,923,060 A | 12/1975 | Ellinwood, Jr. |
| 3,924,819 A | 12/1975 | Lapinskas |
| 4,003,379 A | 1/1977 | Ellinwood, Jr. |
| 4,055,175 A | 10/1977 | Clemens et al. |
| 4,076,182 A | 2/1978 | Stites |
| 4,151,845 A | 5/1979 | Clemens |
| 4,360,019 A | 11/1982 | Portner |
| 4,387,863 A | 6/1983 | Edmonston |
| 4,601,707 A | 7/1986 | Albisser et al. |
| 4,629,145 A | 12/1986 | Graham |
| 4,667,896 A | 5/1987 | Frey et al. |
| 4,685,903 A | 8/1987 | Cable et al. |
| 4,725,010 A | 2/1988 | Lotamer |

(Continued)

FOREIGN PATENT DOCUMENTS

| | | |
|---|---|---|
| WO | WO-01/52935 | 7/2001 |
| WO | WO-01/54753 | 8/2001 |

(Continued)

OTHER PUBLICATIONS

U.S. Appl. No. 12/147,467, Notice of Allowance mailed Sep. 30, 2011.

(Continued)

*Primary Examiner* — Kerri McNally
(74) *Attorney, Agent, or Firm* — Jackson & Co., LLP (57) ABSTRACT

A monitoring apparatus is disclosed which includes a receiver unit for receiving data and outputting a first alert signal based on the received data; and a docking unit comprising a converter unit which converts the first alert signal when the receiver unit is connected to the docking unit.

20 Claims, 7 Drawing Sheets

U.S. PATENT DOCUMENTS

| | | |
|---|---|---|
| 4,802,638 A | 2/1989 | Burger et al. |
| 4,886,505 A | 12/1989 | Haynes et al. |
| 5,019,096 A | 5/1991 | Fox, Jr. et al. |
| 5,067,665 A | 11/1991 | LoStracco et al. |
| 5,097,834 A | 3/1992 | Skrabal |
| 5,109,577 A | 5/1992 | Young |
| 5,209,414 A | 5/1993 | Clemens et al. |
| 5,236,143 A | 8/1993 | Dragon |
| 5,237,993 A | 8/1993 | Skrabal |
| 5,250,023 A | 10/1993 | Lee |
| 5,266,359 A | 11/1993 | Spielvogel |
| 5,344,411 A | 9/1994 | Domb et al. |
| 5,349,852 A | 9/1994 | Kamen et al. |
| 5,390,671 A | 2/1995 | Lord et al. |
| 5,437,656 A | 8/1995 | Shikani et al. |
| 5,451,424 A | 9/1995 | Solomon et al. |
| 5,526,844 A | 6/1996 | Kamen et al. |
| 5,533,389 A | 7/1996 | Kamen et al. |
| 5,558,640 A | 9/1996 | Pfeiler |
| 5,569,186 A | 10/1996 | Lord et al. |
| 5,593,852 A | 1/1997 | Heller et al. |
| 5,599,321 A | 2/1997 | Conway et al. |
| 5,601,435 A | 2/1997 | Quy |
| 5,662,904 A | 9/1997 | Ferguson et al. |
| 5,673,691 A | 10/1997 | Abrams et al. |
| 5,822,715 A | 10/1998 | Worthington et al. |
| 5,899,855 A | 5/1999 | Brown |
| 5,918,603 A | 7/1999 | Brown |
| 5,925,021 A | 7/1999 | Castellano et al. |
| 5,954,643 A | 9/1999 | VanAntwerp et al. |
| 5,956,501 A | 9/1999 | Brown |
| 5,975,120 A | 11/1999 | Novosel |
| 5,988,545 A | 11/1999 | King |
| 6,083,248 A | 7/2000 | Thompson |
| 6,134,461 A | 10/2000 | Say et al. |
| 6,175,752 B1 | 1/2001 | Say et al. |
| 6,233,539 B1 | 5/2001 | Brown |
| 6,248,067 B1 | 6/2001 | Causey et al. |
| 6,254,586 B1 | 7/2001 | Mann et al. |
| 6,284,478 B1 | 9/2001 | Heller et al. |
| 6,379,301 B1 | 4/2002 | Worthington et al. |
| 6,427,088 B1 | 7/2002 | Bowman, IV et al. |
| 6,471,689 B1 | 10/2002 | Joseph et al. |
| 6,482,156 B2 | 11/2002 | Iliff |
| 6,484,045 B1 | 11/2002 | Holker et al. |
| 6,485,461 B1 | 11/2002 | Mason et al. |
| 6,554,798 B1 | 4/2003 | Mann et al. |
| 6,558,321 B1 | 5/2003 | Burd et al. |
| 6,562,001 B2 | 5/2003 | Lebel et al. |
| 6,564,105 B2 | 5/2003 | Starkweather et al. |
| 6,571,128 B2 | 5/2003 | Lebel et al. |
| 6,577,899 B2 | 6/2003 | Lebel et al. |
| 6,585,644 B2 | 7/2003 | Lebel et al. |
| 6,598,824 B2 | 7/2003 | Schmidt |
| 6,635,014 B2 | 10/2003 | Starkweather et al. |
| 6,641,562 B1 | 11/2003 | Peterson |
| 6,648,821 B2 | 11/2003 | Lebel et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,692,457 B2 | 2/2004 | Flaherty |
| 6,694,191 B2 | 2/2004 | Starkweather et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,733,446 B2 | 5/2004 | Lebel et al. |
| 6,736,797 B1 | 5/2004 | Larsen et al. |
| 6,740,059 B2 | 5/2004 | Flaherty |
| 6,740,075 B2 | 5/2004 | Lebel et al. |
| 6,741,877 B1 | 5/2004 | Shults et al. |
| 6,744,350 B2 | 6/2004 | Blomquist |
| 6,749,587 B2 | 6/2004 | Flaherty |
| 6,758,810 B2 | 7/2004 | Lebel et al. |
| 6,768,425 B2 | 7/2004 | Flaherty et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,830,558 B2 | 12/2004 | Flaherty et al. |
| 6,852,104 B2 | 2/2005 | Blomquist |
| 6,862,465 B2 | 3/2005 | Shults et al. |
| 6,873,268 B2 | 3/2005 | Lebel et al. |
| 6,882,940 B2 | 4/2005 | Potts et al. |
| 6,887,270 B2 | 5/2005 | Miller et al. |
| 6,896,666 B2 | 5/2005 | Kochamaba et al. |
| 6,902,207 B2 | 6/2005 | Lickliter |
| 6,916,159 B2 | 7/2005 | Rush et al. |
| 6,931,327 B2 | 8/2005 | Goode, Jr. et al. |
| 6,936,006 B2 | 8/2005 | Sabra |
| 6,946,446 B2 | 9/2005 | Ma et al. |
| 6,950,708 B2 | 9/2005 | Bowman, IV et al. |
| 6,958,705 B2 | 10/2005 | Lebel et al. |
| 6,960,192 B1 | 11/2005 | Flaherty et al. |
| 6,974,437 B2 | 12/2005 | Lebel et al. |
| 7,003,336 B2 | 2/2006 | Holker et al. |
| 7,018,360 B2 | 3/2006 | Flaherty et al. |
| 7,024,245 B2 | 4/2006 | Lebel et al. |
| 7,029,455 B2 | 4/2006 | Flaherty |
| 7,034,677 B2 | 4/2006 | Steinthal et al. |
| 7,052,251 B2 | 5/2006 | Nason et al. |
| 7,052,472 B1 | 5/2006 | Miller et al. |
| 7,066,922 B2 | 6/2006 | Angel et al. |
| 7,074,307 B2 | 7/2006 | Simpson et al. |
| 7,077,328 B2 | 7/2006 | Krishnaswamy et al. |
| 7,079,977 B2 | 7/2006 | Osorio et al. |
| 7,081,195 B2 | 7/2006 | Simpson et al. |
| 7,108,778 B2 | 9/2006 | Simpson et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,137,964 B2 | 11/2006 | Flaherty |
| 7,144,384 B2 | 12/2006 | Gorman et al. |
| 7,155,112 B2 | 12/2006 | Uno et al. |
| 7,167,818 B2 | 1/2007 | Brown |
| 7,171,274 B2 | 1/2007 | Starkweather et al. |
| 7,171,312 B2 | 1/2007 | Steinthal et al. |
| 7,192,450 B2 | 3/2007 | Brauker et al. |
| 7,226,278 B2 | 6/2007 | Nason et al. |
| 7,226,978 B2 | 6/2007 | Tapsak et al. |
| 7,229,042 B2 | 6/2007 | Thebault et al. |
| 7,267,665 B2 | 9/2007 | Steil et al. |
| 7,276,029 B2 | 10/2007 | Goode, Jr. et al. |
| 7,303,549 B2 | 12/2007 | Flaherty et al. |
| 7,310,544 B2 | 12/2007 | Brister et al. |
| 7,364,568 B2 | 4/2008 | Angel et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,424,318 B2 | 9/2008 | Brister et al. |
| 7,429,258 B2 | 9/2008 | Angel et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,645,263 B2 | 1/2010 | Angel et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,711,402 B2 | 5/2010 | Shults et al. |
| 7,713,574 B2 | 5/2010 | Brister et al. |
| 7,715,893 B2 | 5/2010 | Kamath et al. |
| 8,085,151 B2 * | 12/2011 | Jennewine ............ 340/573.1 |
| 2002/0016719 A1 | 2/2002 | Nemeth et al. |
| 2002/0106709 A1 | 8/2002 | Potts et al. |

| | | |
|---|---|---|
| 2002/0107476 A1 | 8/2002 | Mann et al. |
| 2002/0147135 A1 | 10/2002 | Schnell |
| 2002/0193679 A1 | 12/2002 | Malave et al. |
| 2003/0023317 A1 | 1/2003 | Brauker et al. |
| 2003/0032874 A1 | 2/2003 | Rhodes et al. |
| 2003/0060753 A1 | 3/2003 | Starkweather et al. |
| 2003/0065308 A1 | 4/2003 | Lebel et al. |
| 2003/0069541 A1 | 4/2003 | Gillis et al. |
| 2003/0073414 A1 | 4/2003 | P. Capps |
| 2003/0114836 A1 | 6/2003 | Estes et al. |
| 2003/0122021 A1 | 7/2003 | McConnell et al. |
| 2003/0130616 A1 | 7/2003 | Steil et al. |
| 2003/0144362 A1 | 7/2003 | Utterberg et al. |
| 2003/0175323 A1 | 9/2003 | Utterberg et al. |
| 2003/0176933 A1 | 9/2003 | Lebel et al. |
| 2003/0212379 A1 | 11/2003 | Bylund et al. |
| 2003/0217966 A1 | 11/2003 | Tapsak et al. |
| 2004/0011671 A1 | 1/2004 | Shults et al. |
| 2004/0045879 A1 | 3/2004 | Shults et al. |
| 2004/0122530 A1 | 6/2004 | Hansen et al. |
| 2004/0135684 A1 | 7/2004 | Steinthal et al. |
| 2004/0155770 A1 | 8/2004 | Nelson et al. |
| 2004/0186362 A1 | 9/2004 | Brauker et al. |
| 2004/0193090 A1 | 9/2004 | Lebel et al. |
| 2004/0199059 A1 | 10/2004 | Brauker et al. |
| 2004/0210180 A1 | 10/2004 | Altman |
| 2004/0210208 A1 | 10/2004 | Paul et al. |
| 2004/0225338 A1 | 11/2004 | Lebel et al. |
| 2004/0254433 A1 | 12/2004 | Brandis et al. |
| 2005/0004439 A1 | 1/2005 | Shin et al. |
| 2005/0010269 A1 | 1/2005 | Lebel et al. |
| 2005/0027180 A1 | 2/2005 | Goode, Jr. et al. |
| 2005/0031689 A1 | 2/2005 | Shults et al. |
| 2005/0038332 A1 | 2/2005 | Saidara et al. |
| 2005/0043598 A1 | 2/2005 | Goode, Jr et al. |
| 2005/0065464 A1 | 3/2005 | Talbot et al. |
| 2005/0090607 A1 | 4/2005 | Tapsak et al. |
| 2005/0112169 A1 | 5/2005 | Brauker et al. |
| 2005/0113653 A1 | 5/2005 | Fox et al. |
| 2005/0119540 A1 | 6/2005 | Potts et al. |
| 2005/0143635 A1 | 6/2005 | Kamath et al. |
| 2005/0171512 A1 | 8/2005 | Flaherty |
| 2005/0176136 A1 | 8/2005 | Burd et al. |
| 2005/0181010 A1 | 8/2005 | Hunter et al. |
| 2005/0182306 A1 | 8/2005 | Sloan |
| 2005/0182366 A1 | 8/2005 | Vogt et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0203461 A1 | 9/2005 | Flaherty et al. |
| 2005/0238507 A1 | 10/2005 | DiIanni et al. |
| 2005/0245795 A1 | 11/2005 | Goode, Jr. et al. |
| 2005/0245799 A1 | 11/2005 | Brauker et al. |
| 2005/0261667 A1 | 11/2005 | Crank et al. |
| 2006/0001551 A1* | 1/2006 | Kraft et al. ............... 340/870.16 |
| 2006/0015020 A1 | 1/2006 | Neale et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0041229 A1 | 2/2006 | Garibotto et al. |
| 2006/0065772 A1 | 3/2006 | Grant et al. |
| 2006/0095020 A1 | 5/2006 | Casas et al. |
| 2006/0173406 A1 | 8/2006 | Hayes et al. |
| 2006/0173444 A1 | 8/2006 | Choy et al. |
| 2006/0178633 A1 | 8/2006 | Garibotto et al. |
| 2006/0222566 A1 | 10/2006 | Brauker et al. |
| 2006/0224141 A1 | 10/2006 | Rush et al. |
| 2006/0282290 A1 | 12/2006 | Flaherty et al. |
| 2007/0016381 A1 | 1/2007 | Kamath et al. |
| 2007/0060869 A1 | 3/2007 | Tolle et al. |
| 2007/0060870 A1 | 3/2007 | Tolle et al. |
| 2007/0060871 A1 | 3/2007 | Istoc et al. |
| 2007/0093786 A1 | 4/2007 | Goldsmith et al. |
| 2007/0100222 A1* | 5/2007 | Mastrototaro et al. ........ 600/365 |
| 2007/0118405 A1 | 5/2007 | Campbell et al. |
| 2007/0128682 A1 | 6/2007 | Rosman et al. |
| 2007/0129621 A1 | 6/2007 | Kellogg et al. |
| 2007/0163880 A1 | 7/2007 | Woo et al. |
| 2007/0191702 A1 | 8/2007 | Yodfat et al. |
| 2007/0203966 A1 | 8/2007 | Brauker et al. |
| 2007/0208246 A1* | 9/2007 | Brauker et al. ............... 600/365 |
| 2007/0213657 A1 | 9/2007 | Jennewine et al. |
| 2007/0219480 A1 | 9/2007 | Kamen et al. |
| 2007/0219597 A1 | 9/2007 | Kamen et al. |
| 2007/0235331 A1 | 10/2007 | Simpson et al. |
| 2007/0255114 A1* | 11/2007 | Ackermann et al. .......... 600/300 |
| 2007/0299409 A1 | 12/2007 | Whitbourne et al. |
| 2008/0004515 A1 | 1/2008 | Jennewine et al. |
| 2008/0004601 A1 | 1/2008 | Jennewine et al. |
| 2008/0018480 A1 | 1/2008 | Sham |
| 2008/0021666 A1 | 1/2008 | Goode, Jr. et al. |
| 2008/0033254 A1 | 2/2008 | Kamath et al. |
| 2008/0045824 A1 | 2/2008 | Tapsak et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0093447 A1 | 4/2008 | Johnson et al. |
| 2008/0108942 A1 | 5/2008 | Brister et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode. Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0269687 A1 | 10/2008 | Chong et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0069650 A1 | 3/2009 | Jennewine et al. |

| | | |
|---|---|---|
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0099436 A1 | 4/2009 | Brister et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |
| 2010/0292634 A1 | 11/2010 | Kircher et al. |

FOREIGN PATENT DOCUMENTS

| | | |
|---|---|---|
| WO | WO-2006/037109 | 4/2006 |
| WO | WO-2007/101260 | 9/2007 |
| WO | WO-2008/003003 | 1/2008 |
| WO | WO-2008/005780 | 1/2008 |

OTHER PUBLICATIONS

U.S. Appl. No. 12/147,467, Office Action mailed Aug. 10, 2011.
U.S. Appl. No. 12/147,467, Office Action mailed Jan. 21, 2011.
U.S. Appl. No. 12/147,467, Office Action mailed Oct. 5, 2010.

* cited by examiner

SIGNAL CONVERTING CRADLE FOR MEDICAL CONDITION MONITORING AND MANAGEMENT SYSTEM

RELATED APPLICATIONS

The present application is a continuation of U.S. patent application Ser. No. 12/147,467 filed Jun. 26, 2008, now U.S. Pat. No. 8,085,151, which claims priority to U.S. provisional application No. 60/946,760 filed Jun. 28, 2007, the disclosures of each of which are incorporated herein by reference for all purposes.

BACKGROUND

The present disclosure relates to a device for use with a medical condition monitoring and management system. Specifically, the present disclosure relates to a device for receiving a signal from a medical condition monitoring and management system and converting the received signal into a signal chosen by the user.

Detection of the level of analytes, such as glucose, lactate, oxygen, and the like, in certain individuals is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

Devices have been developed for continuous or automatic monitoring of analytes, such as glucose, in the bodily fluids of a user. These devices allow a user to monitor his or her analyte levels and can further alert the user if the analyte levels reach, or fall below, a predetermined threshold level. If an individual is using such an analyte monitoring device, it is also important to detect any malfunction within the monitoring device. Some examples of such devices are illustrated in U.S. Pat. No. 6,175,752, and in US Patent Application Publication No. 2004/0186365 filed Dec. 26, 2003 entitled "Continuous Glucose Monitoring System and Methods of Use". Devices and systems for management of the analyte level may also be included in the analyte monitoring system. An example of an analyte management system is an insulin pump, which may manage the analyte level by delivering a dose of insulin to the user in response to the glucose levels of the user.

In some instances, a user's analyte level may become so low that the user may feel lightheaded, disoriented or confused. In these instances, the analyte monitoring system must be sufficiently loud, so as to alert the user to the potentially dangerous condition and allow the user to correct the problem. A user is particularly vulnerable to the above scenario during nighttime or other sleep periods. A user whose analyte levels severely drop may have a difficult time hearing the alarm, especially if the user is already asleep.

One solution to the above problem is to integrate larger and more powerful speakers, or amplifiers, directly into the analyte monitoring device. However, this solution may unnecessarily increase the size and circuit complexity of the device. Additionally, directly integrating the speakers or amplifiers into the analyte monitoring device will result in an increased cost of the device.

As a result, there is need of a low cost system, which does not affect the size and circuit complexity of the analyte monitoring device.

SUMMARY

Exemplary embodiments of the present disclosure overcome the above disadvantages and other disadvantages not described above and provide advantages which will be apparent from the following description of exemplary embodiments of the disclosure. Also, the present disclosure is not required to overcome the disadvantages described above.

According to an aspect of the present disclosure, there is provided a monitoring apparatus, comprising, a receiver unit which receives medical data of a patient and outputs a first alert signal based on the received data, and a docking unit comprising a converter unit which converts the first alert signal when the receiver unit is connected to the docking unit.

In one aspect of the present disclosure, the received medical data is data corresponding to the analyte level of a patient. According to another aspect of the present disclosure, the receiver unit outputs the first alert signal if the analyte level of the patient reaches a predetermined threshold level.

According to another aspect of the present disclosure, there is provided a monitoring apparatus, comprising, a sensor for monitoring an analyte level of a user, a receiver unit which receives data from the sensor and indicates the level of the analyte, wherein the receiver unit outputs a first alert signal if the analyte level reaches a predetermined threshold level, and a docking unit comprising a converter unit which converts the first alert signal when the receiver unit is connected to the docking unit.

According to one aspect of the present disclosure, the converter unit converts the first alert signal into a second alert signal. According to another aspect of the present disclosure, the first alert signal output by the receiver unit is an auditory signal, and the second alert signal generated by the converter unit is a louder auditory signal. According to this aspect, the first alert signal may be amplified to generate the second alert signal. Alternatively, the converter unit of the above-described aspect of the present disclosure, may replace the first alert signal with the second alert signal.

According to another aspect of the present disclosure, the monitoring apparatus may further comprise a recording medium for recording a sound to be used as the second alert signal.

In another aspect, the one or more of the first or second alert signal may be downloaded from a remote location or device over a data connection such as a local area network, the internet and the like.

According to yet another aspect of the present disclosure, the docking unit of the monitoring apparatus further comprises a charging unit for charging the power supply of the receiver unit when the receiver unit is connected to the docking unit.

According to another aspect of the present disclosure, the docking unit of the monitoring apparatus may further comprise a light control unit, which regulates a light source based on the first alert signal. According to this aspect, the light source may be an external light source.

BRIEF DESCRIPTION OF THE DRAWINGS

The above and other features and advantages of the present disclosure will become more apparent from detailed exemplary embodiments set forth hereinafter with reference to the attached drawings in which.

DETAILED DESCRIPTION

The present disclosure will now be described more fully with reference to the accompanying figures, in which exemplary embodiments of the disclosure are shown. The figures referred to herein are not necessarily drawn to scale, with some components and features being exaggerated for clarity. Like reference numerals in the figures denote like elements.

It is to be understood that the terminology used herein is for the purpose of describing particular embodiments only, and is not intended to be limiting, since the scope of the present disclosure will be limited only by the appended claims. Unless defined otherwise, all technical and scientific terms used herein have the same meaning as commonly understood by one of ordinary skill in the art to which this disclosure belongs. It must be noted that as used herein and in the appended claims, the singular forms "a," "an," and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Figure 1:
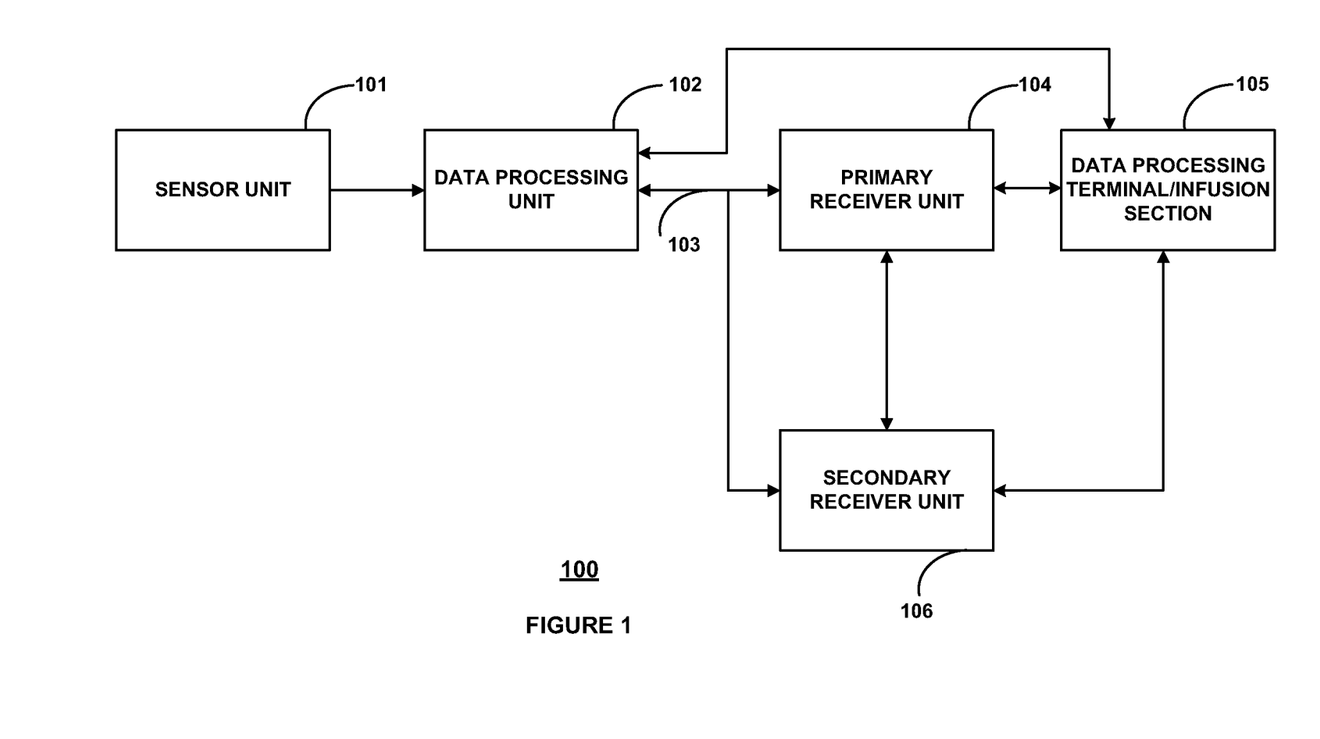
FIG. 1 is a block diagram of an embodiment of a data monitoring and management system according to the present disclosure.

FIG. 1 shows a data monitoring and management system such as, for example, an analyte (e.g., glucose) monitoring system 100 in accordance with certain embodiments. Embodiments of the subject disclosure are further described primarily with respect to glucose monitoring devices and systems, and methods of glucose detection, for convenience only and such description is in no way intended to limit the scope of the disclosure. It is to be understood that the analyte monitoring system may be configured to monitor a variety of analytes at the same time or at different times.

Additionally, one exemplary embodiment the analyte monitoring system may include an analyte management system, such as an insulin pump. Thus, it is to be understood that the following description is directed to an analyte (for example, glucose) monitoring system for convenience only and such description is in no way intended to limit the scope of the disclosure.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

Analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those exemplary embodiments that monitor more than one analyte, the analytes may be monitored at the same or different times.

Additionally, within the scope of the present disclosure, other physiological or medical conditions or medications may be monitored for treatment, such as for example, monitoring for pain medication, cancer medication, or immunosuppressant medication, nonlimiting examples of which may include cyclosporine, tacrolimus, or corticosteroids.

Moreover, the description herein is directed primarily to electrochemical sensors for convenience only and is in no way intended to limit the scope of the disclosure. Other sensors and sensor systems are contemplated. Such include, but are not limited to, optical sensors, colorimetric sensors, and sensors that detect hydrogen peroxide to infer analyte levels.

Referring to FIG. 1, the analyte monitoring system 100 includes a sensor 101, a data processing unit 102 connectable to the sensor 101, and a primary receiver unit 104, which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104 and/or the data processing terminal 105 and/or optionally the secondary receiver unit 106 and/or the docking unit 300, which is described in greater detail below.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. In certain embodiments the secondary receiver unit 106 may be a defeatured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104.

The primary and secondary receiver units 104 and 106 may also include a docking portion to be mated with a docking unit for placement by, e.g., the bedside for night time monitoring, and/or a bi-directional communication device. The docking unit will be described in greater detail below.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 performs data processing functions, where such functions may include but are not limited to, filtering and encoding of data signals, each of which corresponds to a sampled analyte level of the user, for transmission to a receiver unit (104 or 106) via the communication link 103.

Figure 2:
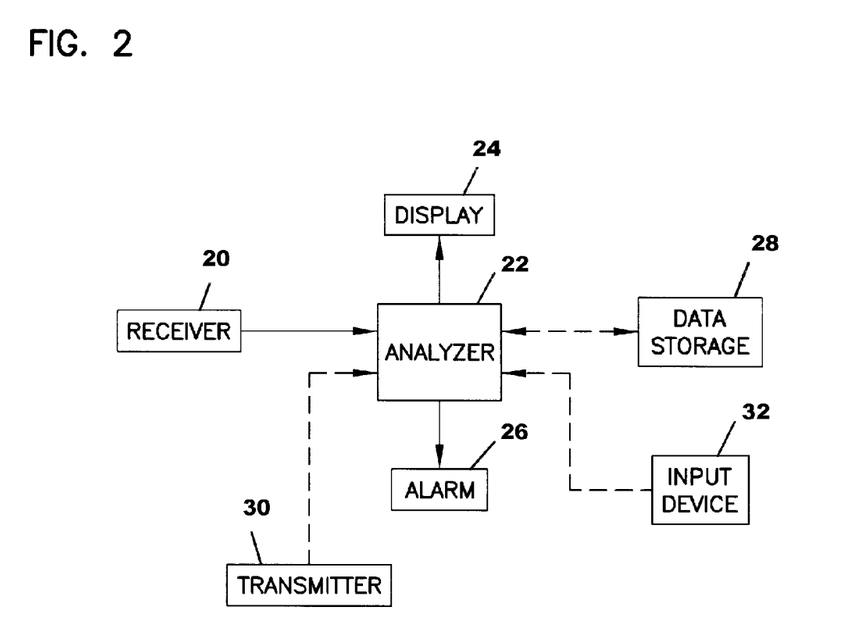
FIG. 2 is a block diagram of one exemplary embodiment of a receiver unit according to the present disclosure.

An exemplary embodiment of the receiver unit is illustrated in block form in FIG. 2, and includes a receiver 20 to receive data from the data processing unit 102, an analyzer 22 to evaluate the data, a display 24 to provide information to the user, and an alarm system 26 to warn the user when a condition arises. The receiver unit (104 or 106) may also optionally include data storage 28, a transmitter 30 and an input device 32.

In one exemplary embodiment, the alarm system 26 of a receiver unit (104 or 106) is triggered when the analyte level of a user equals, or falls below, a predetermined threshold analyte level. Each condition of the user that can trigger an alarm may have a different alarm activation condition.

The alarm system 26 may also contain one or more individual alarms. Each of the alarms may be individually activated to indicate one or more conditions associated with an analyte. Additionally, the analyte monitoring system 100 may include several threshold levels for each analyte to be measured, and an individual alarm corresponding to each threshold level. When the alarm is activated, the alarm system 26 outputs an alert signal corresponding to the activated alarm. In some embodiments, the alarms are auditory, e.g., with a different tone, note or volume indicating different conditions. In another exemplary embodiment of the present disclosure, various tones of the alarm system 26 may indicate varying urgency levels of a user's need to correct a problem, such as when the analyte level is dangerously low. Additionally, other exemplary embodiments of the present disclosure include an analyte monitoring system 100 which may predict future analyte levels. For example, the analyte monitoring system 100 may detect the rate of change of analyte levels in the user and predict the analyte level of the user at a future point in time. As such, certain types of alarms may warn the user that he will reach a predetermined analyte threshold level within a certain time, if no action is taken.

The varying types of alarms described above may be pre-associated with various conditions by default, may be set by the user or may be set by any other authorized person. This allows the user, or another authorized person, to customize the device according to the needs, or treatment requirements of the user. For example, some users will want to have a series of escalating alarms to respond to varying glucose levels. In this example, a user may set a medium level audio alarm clock type of alarm to indicate a projected low analyte level 30 minutes in advance, followed by a maximum level audio alarm recorded in a parent's voice calling the user's name to indicate that a low threshold has been reached, followed by the maximum level audio alarm accompanied by flashing lights when the user reaches an analyte level 10 mg/dL below the low threshold.

Figure 3A:
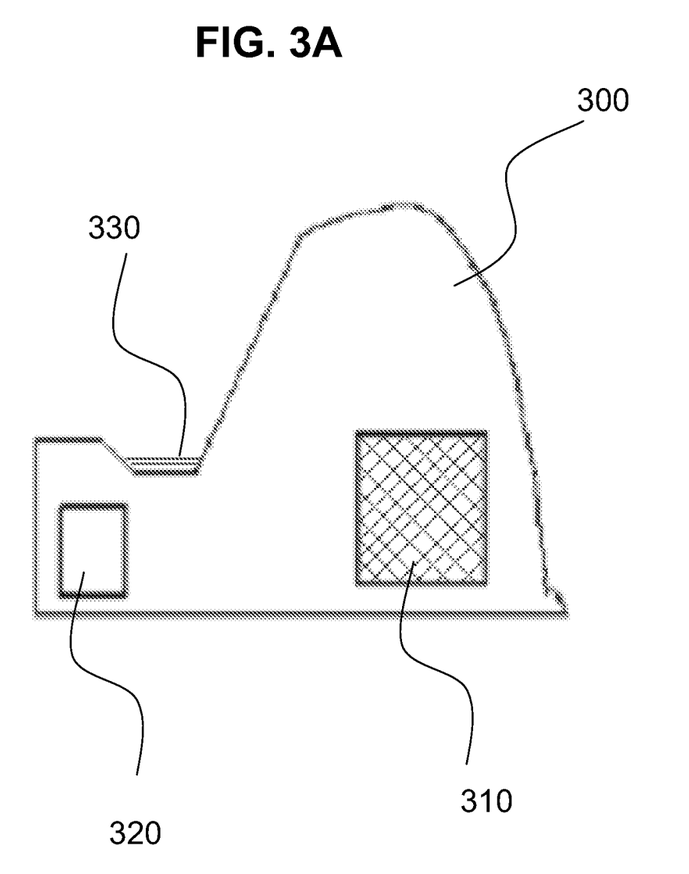
FIG. 3A is a side view of an exemplary embodiment of a docking unit according to the present disclosure.

With regard to FIG. 3A, there is illustrated a side view of a docking unit 300 in accordance with an exemplary embodiment of the present disclosure. As described above, the receiver unit (104 or 106) may be mated with the docking unit 300. As shown in FIG. 3A, the docking unit 300 may include a speaker 310, a recording medium 320 and a connector 330. In one exemplary embodiment, the docking unit 300 may be used to charge the receiver unit (104 or 106). Additionally, in one exemplary embodiment the speaker 310 can be a plurality of speakers.

The interrelationship between the docking unit 300 and the primary and secondary receiver units (104 and 106) will now be described. In one exemplary embodiment, the primary receiver unit 104 may provide functions similar to those of the docking unit 300. That is, the primary receiver unit 104 may include speakers and louder alarm settings. With regard to those features of the primary receiver 104 and the docking unit 300 that overlap, the docking unit simply provides an additional alarm capability. The docking unit 300 may also provide additional features, which may not be included in the primary receiver unit 104, as described below.

With regard to the secondary receiver unit 106, as mentioned above, the secondary receiver unit 106 may include a limited or minimal number of functions and features as compared with the primary receiver unit 104. Thus, with relation to the secondary receiver unit 106, the docking unit 300 provides the user with the ability to split functionality between the docking unit 300 and the receiver unit 104, as desired. For example, by removing the large speakers and/or amplifiers from the receiver unit 104, the receiver unit 104 may be made lighter, smaller and less expensive, while retaining the ability to effectively awaken or alert the user as needed. It is to be understood that any, all or none of the features of the secondary receiver unit 104 may be transferred to the docking unit 300.

Figure 3B:
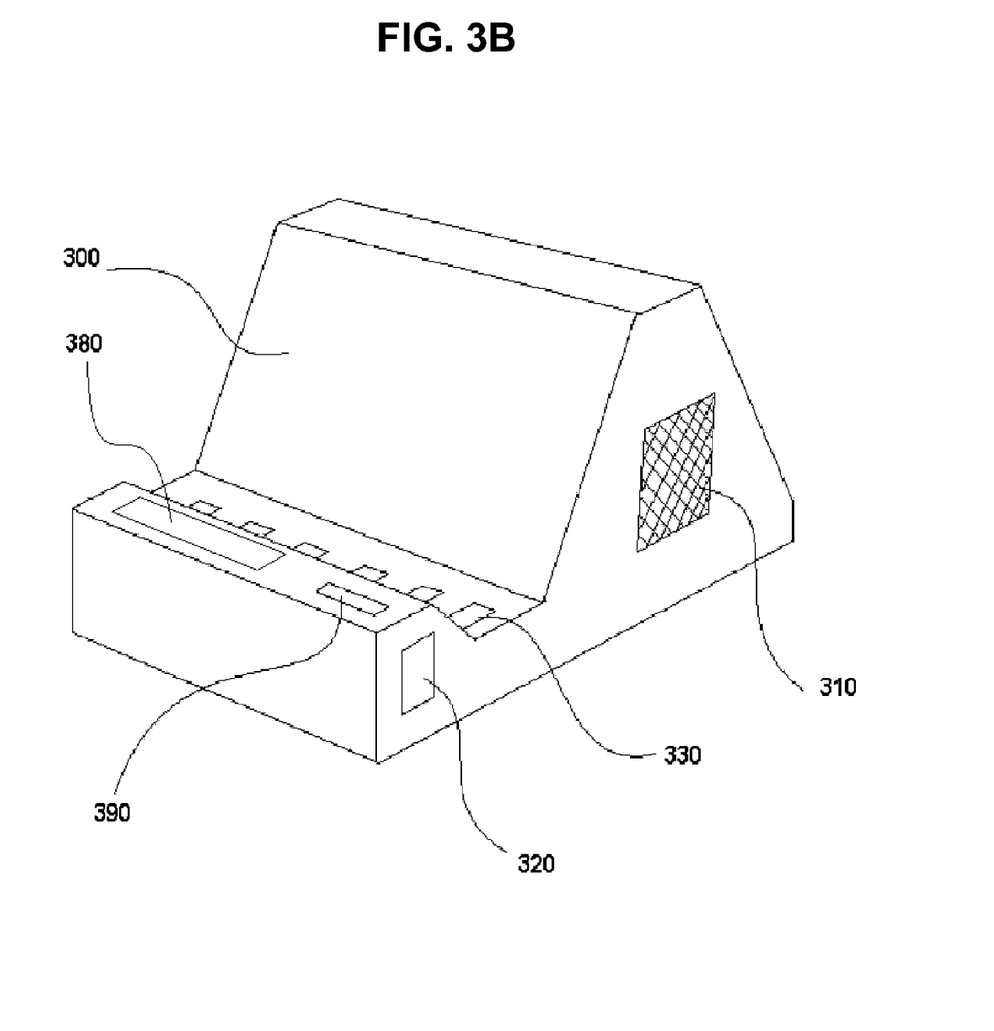
FIG. 3B is a profile view of an exemplary embodiment of a docking unit according to the present disclosure.

FIG. 3B shows a profile view of the docking unit 300 illustrated in FIG. 3A. According to one exemplary embodiment, the docking unit 300 may further include an input device 380 and a charge indicator 390, such as for example, a light which indicates that the receiver unit (104 or 106) is charging.

In one exemplary embodiment, the connector 330 is used as a mating station between a docking portion of the receiver unit (104 or 106) and the docking unit 300. In another exemplary embodiment, the connector 330 may be used to communicate between the docking unit 300 and/or the receiver units (104 or 106) and/or the sensor 101 and/or any other device, such as a computer. In one exemplary embodiment, the connector 330 of the docking unit 300 may be configured for bi-directional communication with the above-listed devices. Varying types of connections which may be used are described in greater detail below, and include wired and wireless protocols. In this exemplary embodiment, when the receiver unit (104 or 106) is connected to the connector 330 of the docking unit 300, the docking unit 300 receives the alert signal output by the alarm system 26 of the receiver unit (104 or 106), converts the alert signal of the receiver unit (104 or 106) into a second alert signal and outputs the second alert signal to the speaker 310. The conversion can be accomplished using a converter (not shown) located within the docking unit 300.

Figure 3C:
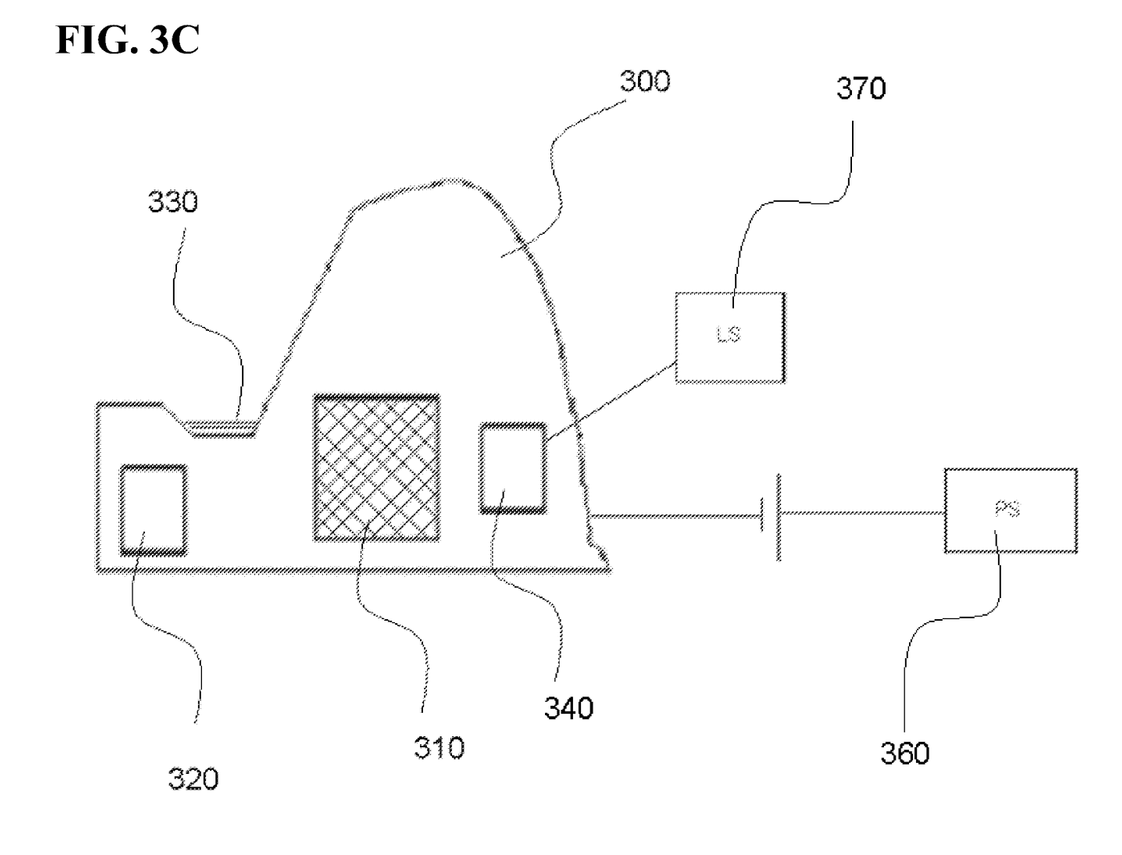
FIG. 3C is another exemplary embodiment of a docking unit according to the present disclosure.
Figure 3D:
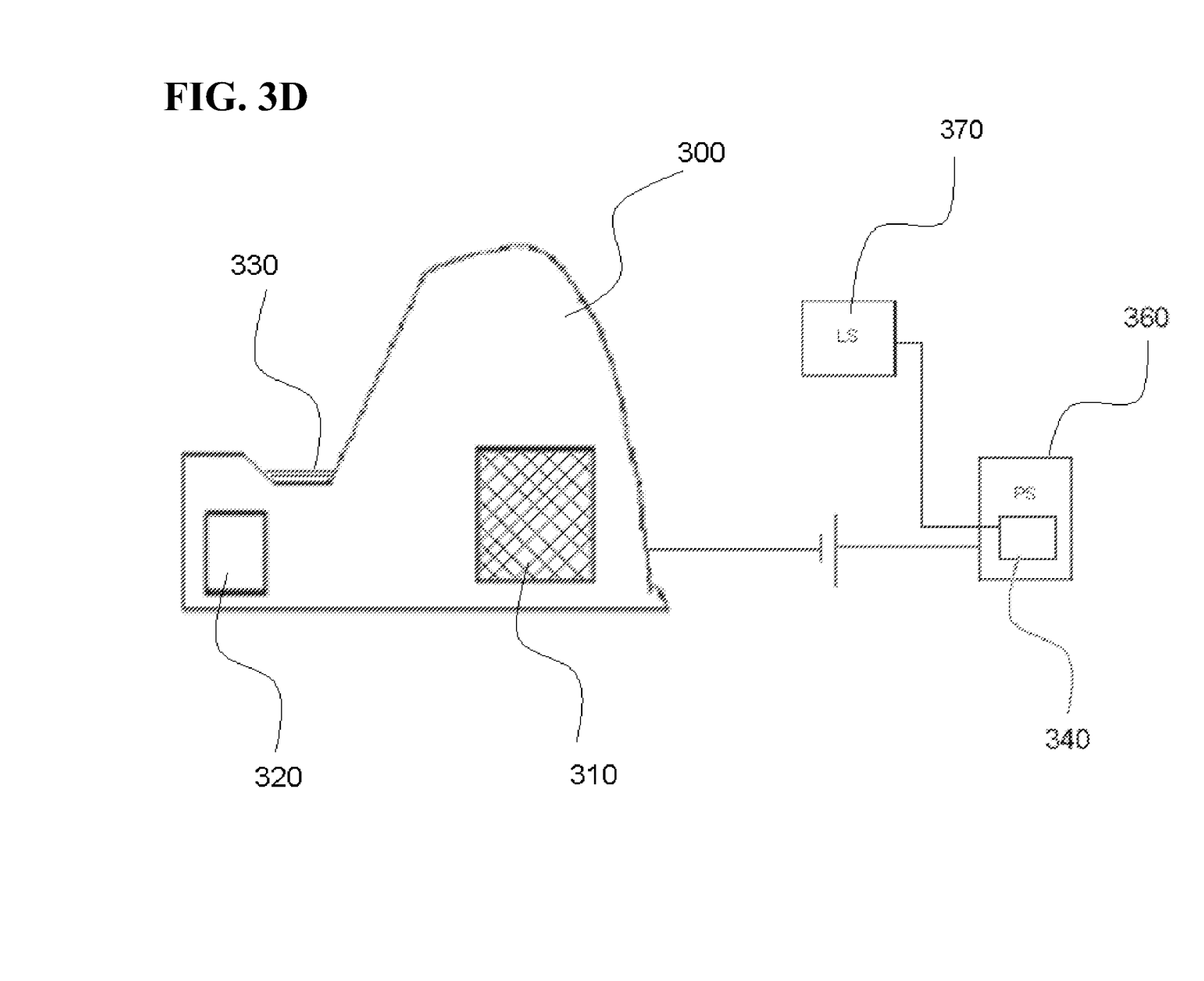
FIG. 3D is another exemplary embodiment of a docking unit according to the present disclosure.

As shown in FIGS. 3C and 3D, in one exemplary embodiment, the docking unit 300 of FIG. 3A may be connected to the power supply 360. In this exemplary embodiment, the docking unit 300 may further include a control circuit 340 for controlling a light source 370. In one exemplary embodiment, the light source 370 may be provided directly on the docking unit 300 or may be an external light source. Similarly, the control circuit 340 may be provided directly on the docking unit 300, or may be an outside circuit. (Compare FIG. 3C and FIG. 3D). In embodiments where the light source 370 is an external light source, such as a lamp, the control unit 340 may be wirelessly or physically connected to the external light source 370. Additionally, in one exemplary embodiment, the control unit 340 of the docking unit 300 may turn the light source 370 on and off in accordance with the first or second alert signal.

Figure 4:
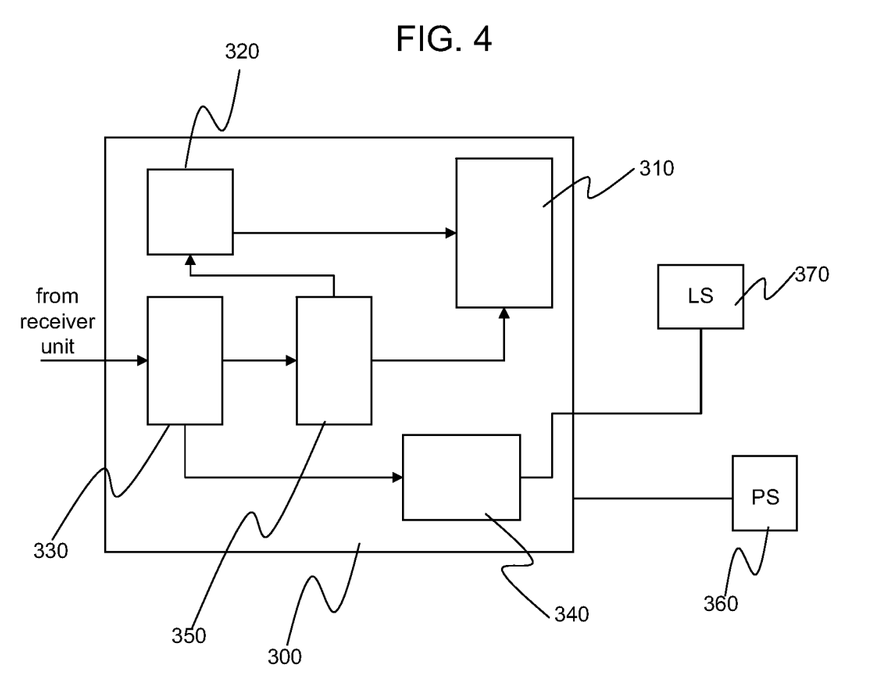
FIG. 4 is a block diagram of one exemplary embodiment of a docking unit according to the present disclosure.

FIG. 4 is a block diagram of the docking unit 300 according to an exemplary embodiment of the present disclosure. Some exemplary functions will now be explained using the block diagram of FIG. 4. In one exemplary embodiment, the connector 330 receives the first alert signal of the alarm system 26 of the receiver unit (104 or 106) and sends it to the converter 350. The converter 350 then amplifies the first alert signal to generate a louder, second alert signal. That is, in this exemplary embodiment, the docking unit 300 amplifies the sound of the alarm, when the alarm is activated in the receiver unit (104 or 106). In one exemplary embodiment, both the receiver unit (104 or 106) and the docking unit 300 emit an auditory alarm. In one exemplary embodiment, the tone of the auditory alarm emitted by the docking unit 300 and the tone of the auditory alarm emitted by the receiver unit (104 or 106) may be the same. In another exemplary embodiment the tone of the auditory alarm emitted by the docking unit 300 and the receiver unit (104 or 106) may be different and clash when emitted.

With further reference to FIG. 4, in another exemplary embodiment of the disclosure, the connector 330 receives the first alert signal output by the receiver unit (104 or 106) and sends it to the converter 350. The converter 350 then outputs the same first alert signal through the speaker 310 of the docking unit 300. In this exemplary embodiment, the speaker 310 of the docking unit 300 has a maximum volume that is louder than the volume of the receiver unit's speakers. As such, the receiver units 104 and 106 are not required to have powerful speakers. Reducing the size of the speakers on the receiver units 104 and 106 may allow the receiver units to be more compact, inexpensive, and/or durable.

In yet another exemplary embodiment, the connector 330 may receive the first alert signal output by the receiver unit (104 or 106) and send it to the converter 350. The converter 350 may then replace or otherwise modify the first alert signal with a second alert signal. The converter 350 then outputs the second alert signal through the speaker 310. In one exemplary embodiment, the recoding medium 320 may be used to record an alert message, wherein the recorded message will act as the second alert signal and will replace the first alert signal of the receiver unit (104 or 106). For example, if the analyte monitoring system 100 is to be used for a child, the recorded message may be the voice of a parent or guardian. In another exemplary embodiment, the recorded message may be the voice of a doctor, the voice of a celebrity, or the voice of any other person. Additionally, there may be several recorded messages which correspond to the several possible individual alarms of the alarm system 26 of the receiver unit (104 or 106). Some examples of messages that may correspond to varying alarms may be: "Check glucose!," "Wake up!," "Low glucose!," "Glucose is 50 mg/dL," "High glucose! Check Keytones!," "Check insulin delivery!," "Check pump!" or "Check sensor!." These messages may be pre-programmed into the system, may be customized for a specific user or may be edited by the user. In other embodiments, these messages may be downloaded over a data network such as a local area network, or the internet.

In one exemplary embodiment, the docking unit 300 may also include an input device 380 such as a keypad or keyboard. The input device 380 may allow numeric or alphanumeric input. The input device 380 may also include buttons, keys, or the like which initiate functions of and/or provide input to the docking unit 300. Such functions may include changing the settings, alarm types, volume levels or alarm conditions of the docking unit 300 but are not limited to the above. For example, the user may choose whether a pre-recorded voice will be used as an alarm, choose the volume level and associate that alarm with a specific condition. Additional functions include interaction between the docking unit 300 and a receiver unit (104 or 106), or any other device. For example, as previously mentioned, an alert signal may be any pre-recorded sound. These sounds may be recorded on any medium and then transferred to the docking unit 300, via the connector 330 and the input device 380, to be used as the alert signal. Similarly, alarm conditions and types may be defined for a treatment type, or individual user, using computer software. These predefined settings may also be downloaded to the docking unit 300 via the connector 330 and the input device 380.

In another exemplary embodiment, the input device 380 may be a screen to display the settings to the user. Moreover, the input device 380 may be any combination of the above, including a touch screen for interacting with the docking unit 300 as described above.

The receiver unit (104 or 106) may be connected to the docking unit 300 using any type of connection. For example, the docking unit 300 may be connected to the primary and/or secondary receiver unit (104 and 106) via a physical connection, a wireless connection or both. In one exemplary embodiment, the docking unit 300 may detect the primary and/or secondary receiver (104 or 106), when the receiver units (104 and 106) are within a predetermined distance of the docking unit 300.

In another exemplary embodiment, one receiver unit (104 or 106) may be physically connected to the docking unit, for example while charging. In this exemplary embodiment, the docking unit may still detect the other receiver unit (104 or 106), if that receiver unit is within a predetermined distance of the docking unit 300.

In another exemplary embodiment, the connection between the receiver unit (104 or 106) and the docking unit may be both a physical and wireless connection. That is, the charging function, for example, may be performed via a physical connection, while the receiver unit (104 or 106) may otherwise communicate with the docking unit 300, such as for example sending an alert signal to the docking unit 300, via a wireless connection. It is to be understood that any combination of functions and connection types may be used.

For example, a mini-USB is one component that may provide for a physical connection between the docking unit 300 and the receiver unit (104 or 106), or the docking unit 300 and any other device. The mini-USB can be used to pass electricity into the receiver unit (104 or 106) to charge the battery and can also be used as a conduit to upload and download information between a receiver unit (104 or 106) and the docking unit 300 and/or between the docking unit 300 and a computer, or any other device. It is to be understood that any of these functions may be accomplished using either a physical or wireless connection.

In embodiments where a wireless connection is used, the remote connection may use one or more of: an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements), while avoiding potential data collision and interference.

Accordingly, a monitoring apparatus in one aspect may include a receiver unit which receives medical data of a patient and outputs a first alert signal based on the received data, and a docking unit comprising a converter unit which converts the first alert signal when the receiver unit is connected to the docking unit.

The received medical data may include data corresponding to the analyte level of a patient, and further, where the receiver unit may be configured to output the first alert signal if the analyte level of the patient reaches a predetermined threshold level.

In another aspect, the converter unit may be configured to convert the first alert signal into a second alert signal, where the first alert signal output by the receiver unit may be an auditory signal, and the second alert signal generated by the converter unit may be a louder auditory signal. In another embodiment, the first alert signal may be amplified to generate the second alert signal.

In still another aspect, the converter unit may replace the first alert signal with the second alert signal.

The apparatus may include a recording medium for recording a sound to be used as the second alert signal.

Also, the docking unit may include a charging unit for charging the power supply of the receiver unit when the receiver unit is connected to the docking unit.

Still further, the docking unit may include a light control unit, which regulates a light source based on the first alert signal, where the light source may include an external light source.

A monitoring apparatus in accordance with another aspect includes a sensor for monitoring an analyte level of a user, a receiver unit which receives data from the sensor and indicates the level of the analyte, wherein the receiver unit outputs a first alert signal if the analyte level reaches a predetermined threshold level, and a docking unit comprising a converter unit which converts the first alert signal when the receiver unit is connected to the docking unit.

The converter unit may convert the first alert signal into a second alert signal, where the first alert signal output by the receiver unit may include an auditory signal, and the second alert signal generated by the converter unit may include a louder auditory signal.

Also, the first alert signal may be amplified to generate the second alert signal.

The converting unit may replace the first alert signal with the second alert signal.

The apparatus may include a recording medium for recording a sound to be used as the second alert signal.

The docking unit may include a charging unit for charging the power supply of the receiver unit when the receiver unit is connected to the docking unit.

In another aspect, the docking unit may include a light control unit, which regulates a light source based on the first alert signal, where the light source may be an external light source.

The sensor for monitoring the analyte level of the user may be attached to the user.

Although exemplary embodiments of the present disclosure have been described, it will be understood by those skilled in the art that the present disclosure should not be limited to the described exemplary embodiments, but various changes and modifications can be made within the spirit and the scope of the present disclosure. Accordingly, the scope of the present disclosure is not limited to the described range of the following claims.

What is claimed is:

1. A method, comprising:
    receiving a first medical data of a person and a second medical data of the person;
    outputting, using an alarm system, a first alert signal corresponding to a first medical condition based on the first medical data, wherein the first alert signal comprises a first tone and a unique identifier associated with the person;
    outputting, using the alarm system, a second alert signal corresponding to a second medical condition based on the second medical data, wherein the second alert signal comprises a second tone and the unique identifier associated with the person;
    modifying, using one or more processors, stored alarm settings, a loudness of the first alert signal and the second alert signal, and a tone of the first alert signal and the second alert signal based on user input;
    amplifying, using a docking unit, the first alert signal and the second alert signal when the alarm system is operatively coupled to the docking unit; and
    outputting, using the docking unit, the amplified first tone of the first alert signal and the amplified second tone of the second alert signal.

2. The method of claim 1, wherein one or more of the received first or second medical data is data corresponding to an analyte level of the person.

3. The method of claim 2, including outputting the first alert signal if the analyte level of the person reaches a predetermined threshold level.

4. The method of claim 1, further comprising recording a sound to be used as the second alert signal in a recording medium.

5. The method of claim 1, wherein the first alert signal is output when the first medical data indicates a first glucose level and the second alert signal is output when the second medical data indicates a second glucose level.

6. The method of claim 1, wherein the loudness of the first tone of the first alert signal and the second tone of the second alert signal is less than the loudness of the amplified first tone of the first alert signal and the amplified second tone of the second alert signal.

7. The method of claim 6, further comprising outputting a modified first tone and a modified second tone, wherein the first tone and the modified first tone clash when outputted simultaneously, and wherein the second tone and the modified second tone clash when outputted simultaneously.

8. The method of claim 1, further comprising regulating a light source based on the first alert signal.

9. A method, comprising:
    receiving a level of an analyte of a person;
    outputting, using an alarm system, a first alert signal if the analyte level reaches a first predetermined threshold, wherein the first alert signal comprises a first tone and a unique identifier associated with the person;
    outputting, using the alarm system, a second alert signal if the analyte level reaches a second predetermined threshold, wherein the second alert signal comprises a second tone and the unique identifier associated with the person;
    modifying, using one or more processors, stored alarm settings, a loudness of the first alert signal and the second alert signal, and a tone of the first alert signal and the second alert signal based on user input;
    amplifying, using a docking unit, the first alert signal and the second alert signal when the alarm system is operatively coupled to the docking unit; and
    outputting, using the docking unit, the amplified first tone of the first alert signal and the amplified second tone of the second alert signal.

10. The method of claim 9, further comprising recording a sound to be used as the second alert signal in a recording medium.

11. The method of claim 9, wherein the first predetermined threshold includes a hypoglycemic condition.

12. The method of claim 9, wherein the loudness of the first tone of the first alert signal and the second tone of the second alert signal is less than the loudness of the amplified first tone of the first alert signal and the amplified second tone of the second alert signal.

13. The method of claim 12, further comprising outputting a modified first tone and a modified second tone, wherein the first tone and the modified first tone clash when outputted simultaneously, and wherein the second tone and the modified second tone clash when outputted simultaneously.

14. The method of claim 9, further comprising regulating a light source based on the first alert signal.

15. A method, comprising:
receiving a level of an analyte of a person;
outputting, using an alarm system, a first alert signal if the analyte level reaches a first predetermined threshold, wherein the first alert signal comprises a first tone and a unique identifier associated with the person;
outputting, using the alarm system, a second alert signal if the analyte level reaches a second predetermined threshold, wherein the second alert signal comprises a second tone and the unique identifier associated with the person;
modifying, using one or more processors, stored alarm settings, a loudness of the first alert signal and the second alert signal, and the tone of the first alert signal and the second alert signal;
amplifying, using a docking unit, the first alert signal and the second alert signal when the alarm system is operatively coupled to the docking unit; and
outputting, using the docking unit, the amplified first tone of the first alert signal and the amplified second tone of the second alert signal.

16. The method of claim 15, further comprising recording a sound to be used as the second alert signal in a recording medium.

17. The method of claim 16, further comprising regulating a light source based on the first alert signal.

18. The method of claim 15, wherein the first predetermined threshold includes a hypoglycemic condition.

19. The method of claim 15, wherein the loudness of the first tone of the first alert signal and the second tone of the second alert signal is less than the loudness of the amplified first tone of the first alert signal and the amplified second tone of the second alert signal.

20. The method of claim 19, further comprising outputting a modified first tone and a modified second tone, wherein the first tone and the modified first tone clash when outputted simultaneously, and wherein the second tone and the modified second tone clash when outputted simultaneously.

* * * * *